US007727569B2

(12) United States Patent
Kuwabara et al.

(10) Patent No.: US 7,727,569 B2
(45) Date of Patent: Jun. 1, 2010

(54) METHOD OF DRY FRACTIONATION OF FAT OR OIL

(75) Inventors: Yuji Kuwabara, Izumisano (JP); Nobuaki Kanai, Izumisano (JP); Toshiaki Takahashi, Izumisano (JP); Yoshihiro Yamanaka, Izumisano (JP)

(73) Assignee: Fuji Oil Company, Limited, Osaka (JP)

( * ) Notice: Subject to any disclaimer, the term of this patent is extended or adjusted under 35 U.S.C. 154(b) by 980 days.

(21) Appl. No.: 10/584,623

(22) PCT Filed: Dec. 15, 2004

(86) PCT No.: PCT/JP2004/018711

§ 371 (c)(1),
(2), (4) Date: Jun. 26, 2006

(87) PCT Pub. No.: WO2005/063952

PCT Pub. Date: Jul. 14, 2005

(65) Prior Publication Data

US 2007/0160739 A1 Jul. 12, 2007

(30) Foreign Application Priority Data

Dec. 26, 2003 (JP) ............................ 2003-432274

(51) Int. Cl.

| | |
|---|---|
| ***A23D 7/00*** | (2006.01) |
| ***A23D 9/00*** | (2006.01) |
| ***C11B 7/00*** | (2006.01) |
| ***C07C 51/43*** | (2006.01) |
| ***C07C 53/00*** | (2006.01) |
| ***C08G 63/48*** | (2006.01) |

(52) U.S. Cl. ....................... 426/417; 426/601; 426/607; 426/665; 554/1; 554/175; 554/211

(58) Field of Classification Search ................. 426/607, 426/601, 417, 665; 554/1, 175, 211
See application file for complete search history.

(56) References Cited

U.S. PATENT DOCUMENTS 5,045,243 A 9/1991 Kuwabara et al.

FOREIGN PATENT DOCUMENTS

| | | |
|---|---|---|
| EP | 0 041 300 | 12/1981 |
| EP | 0 651 046 | 5/1995 |
| EP | 0 798 369 | 10/1997 |
| JP | 63-258994 | 10/1988 |
| JP | 2-14290 | 1/1990 |
| JP | 2003-134998 | 5/2003 |
| WO | 96/05279 | 2/1996 |
| WO | 01/96507 | 12/2001 |

OTHER PUBLICATIONS

Translation of Higuchi et al. (JP0258994 A), see Applicant's IDS for JP document.*

Translation of JP 2003-134998, see Applicant's IDS for JP document.*

(Continued)

*Primary Examiner*—Brent T O Hern
(74) *Attorney, Agent, or Firm*—Wenderoth, Lind & Ponack, L.L.P.

(57) ABSTRACT

It is intended to provide a procedure for, in the fractionation of vegetable butter, transesterified fat or oil, isomerized hydrogenated fat or oil, etc. without the use of solvents, obtaining high-concentration component G2U (defined below) by concentrating operation through reduction of the amount of liquid component residue in crystal portion. There is provided a method of dry fractionation of fat or oil characterized in that fat or oil (A) containing components G2U and GU2 is fractionated through crystallization/solid-liquid separation into crystal fraction of concentrated G2U (AF) and liquid fraction of concentrated GU2 (AL), subsequently this crystal fraction (AF) is mixed with liquid G2U-containing fat or oil (B) whose GU2 concentration is lower than that of the liquid fraction (AL) and thereafter the mixture is separated into crystal fraction (BF) and liquid fraction (BL). Provided that G represents a saturated or trans acid form fatty acid residue; U a cis form unsaturated fatty acid residue; and G2U a triglyceride of G2-residue and U1-residue bonded together.

11 Claims, 1 Drawing Sheet

OTHER PUBLICATIONS

International Search Report issued Feb. 15, 2005 in the International (PCT) Application PCT/JP2004/018711 of which the present application is the U.S. National Stage.

Supplementary European Search Report dated May 7, 2008 in EP Application No. 04 80 7070 corresponding to the present U.S. application.

* cited by examiner

METHOD OF DRY FRACTIONATION OF FAT OR OIL

TECHNICAL FIELD

The present invention relates to a method for obtaining fat or oil useful for the production of hard butter by dry fractionation.

BACKGROUND ART

Known methods of fractionation technologies of fat or oil include a solvent fractionation method and dry fractionation method. While the fractionation technology as used herein means a technology for separating fat or oil into a crystal fraction and a liquid fraction by taking advantage of differences in crystallization characteristics, fractionation performance between a crystal fraction and a liquid fraction differs depending on a particular fractionation method. In a solvent fractionation method, fat or oil is dissolved by adding 0.5 to 5 times larger volume of a solvent (such as acetone, hexane and alcohols), and crystals are precipitated by cooling the resulting solution to separate a crystal fraction. The fractionation performance between a crystal fraction and a liquid fraction is quite excellent, and the amount of a residual liquid component in a crystal portion is usually low as compared with a dry fractionation method. However, the production cost by a solvent fractionation method is high as compared with a dry fractionation method since this method requires confirmation for safety ascribed to the use of the solvent.

While yields of a crystal fraction and a liquid fraction can be controlled by a fractionation temperature in a dry fractionation method, the amount of residual liquid components in a crystal fraction is quite high as compared with a solvent fractionation method since no solvent is used for solid-liquid separation by pressing or filter press. Therefore, it has been impossible to reduce the amount of a residual liquid component after solid-liquid separation. While the residual amount of a liquid component largely affects the quality of fat or oil used as hard butter, it has not been easy to solve the problem.

DISCLOSURE OF THE INVENTION

Problem to be Solved by the Invention

Heretofore, the increase in the pressing pressure for solid-liquid separation or the change in kinds of filter clothes (materials, meshes and the like) has been attempted in order to decrease the residual amount of a liquid component in a crystal fraction in a dry fractionation method. However, there is a limit to decrease in the residual amount of a liquid component in a crystal fraction, and the quality of a crystal fraction obtained by a dry fractionation method is not always satisfactory as compared with that of a solvent fractionation method.

Means for Solving the Problem

The present inventors have been studied intensively and, as a result, have been found that a dry fractionation method whose crystal fraction is of good quality with a reduced amount of a liquid component can be completed by mixing liquid fat or oil containing a less major component of a liquid part and a more major component in a crystal part as compared with a fractionated liquid fraction, with a crystal fraction, and subjecting the mixture to press filtration, followed by solid-liquid separation.

That is, the invention is:

(1) A dry fractionation method of fat or oil which comprises the steps of:

fractionating fat or oil (A) containing G2U and GU2 through crystallization/solid-liquid separation into a crystal fraction of concentrated G2U (AF) and a liquid fraction of concentrated GU2 (AL), mixing the crystal fraction (AF) with liquid G2U-containing fat or oil (B) whose GU2 concentration is lower than that of the liquid fraction (AL), and then separating the mixture into a crystal fraction (BF) and a liquid fraction (BL), wherein G represents a saturated or trans acid form fatty acid residue, U represents a cis form unsaturated fatty acid residue, G2U represents a triglyceride of two G-residues and one U-residue bonded together, and GU2 represents a triglyceride of one G-residue and two U-residues bonded together;

(2) The fractionation method according to the above (1), wherein liquid G2U-containing fat or oil (B) whose GU2 concentration is lower than that of the liquid fraction (AL) is the fat or oil (A);

(3) The fractionation method according to the above (1), wherein the liquid fraction (BL) is used by recycling as a part or all of the fat or oil (A);

(4) The fractionation method according to the above (1) or (2), wherein the fat or oil (A) is vegetable butter or a middle-melting point fraction thereof, liquid oil and interesterified oil obtained by selectively introducing a saturated fatty acid to 1,3-positions of fat or oil which is rich in oleic acid at the 2-position, or isomerized hydrogenated oil;

(5) The fractionation method according to the above (3), wherein the vegetable butter is palm oil, shea butter or illipe butter;

(6) The dry fractionation method according to the above (1) or (2), wherein G2U is 1,3-di-saturated-2-unsaturated triglyceride (SUS, where S represents a saturated fatty acid residue and U represents a cis form unsaturated fatty acid residue);

(7) The dry fractionation method according to the above (5), wherein the saturated fatty acid residue (S) has 16 to 22 carbon atoms, and the unsaturated fatty acid residue (U) has 18 carbon atoms;

(8) The fractionation method according to the above (3), wherein the fat or oil (A) is interesterified oil whose starting material is the liquid fraction (AL);

(9) The fractionation method according to the above (1), wherein the mixing ratio of the crystal fraction (AF) to the fat or oil (B) is in the range from 1:1 to 1:4;

(10) The fractionation method according to the above (8), wherein the mixing ratio of the crystal fraction (AF) to the fat or oil (B) is in the range from 1:1 to 1:2;

(11) The fractionation method according to the above (1), wherein the temperature-controlled fat or oil (B) is mixed with a cake of the crystal fraction (AF); and

(12) The dry fractionation method according to the above (1), wherein the crystal fraction (AF) is crushed and mixed with the fat or oil (B).

Effect of the Invention

The residual amount of a liquid component in a crystal fraction can be reduced by fractionating the fat or oil (A) containing G2U and GU2 through crystallization and solid-liquid separation into a crystal fraction (AF) of concentrated G2U and a liquid fraction (AL) of concentrated GU2, and mixing the crystal fraction (AF) with liquid G2U-containing fat or oil (B) whose GU2 concentration is lower than that of the liquid fraction (AL), followed by separating a crystal fraction (BF) from a liquid fraction (BL). As a result, fat or oil of good quality as hard butter can be obtained.

BEST MODE FOR CARRYING OUT THE INVENTION

The fat or oil (A) of the present invention contains G2U and GU2, wherein G represents a saturated or trans acid form fatty acid residue, U represents a cis form unsaturated fatty acid residue, G2U represents a triglyceride of two G-residues and one U-residue bonded together, and GU2 represents a triglyceride of one G-residue and two U-residues bonded together. While any fat or oil may be used so long as the fat or oil contains G2U and GU2, examples thereof include so-called vegetable butter such as palm oil, shea butter and illipe butter, or a middle-melting point fraction thereof, interesterified oil obtained by selectively introducing saturated fatty acids to 1,3-positions of fat or oil which is rich in oleic acid at the 2-position, or isomerized hydrogenated fat or oil so as to enhance the content of trans-acids.

As the interesterified oil, the fat or oil containing G2U and GU2 can be obtained by reacting G (saturated or trans acid form fatty acid) or an ethyl ester thereof with UUU (cis-unsaturated fatty acid) using 1,3-position specific lipase as a catalyst.

As G2U used for hard butter, a symmetrical triglyceride, i.e., 1,3-di-saturated-2-unsaturated triglyceride (SUS: S represents a saturated fatty acid residue and U represents a cis form unsaturated fatty acid residue) is preferable, and examples of the saturated fatty acid of the residue (S) include palmitic acid having 16 carbon atoms, stearic acid having 18 carbon atoms, arachidic acid having 20 carbon atoms and behenic acid having 22 carbon atoms. Examples of the cis form unsaturated fatty acid of the residue (U) include oleic acid having 18 carbon atoms and one double bond, linoleic acid having two double bonds, and linolenic acid having three double bonds. Oleic acid is preferable among them as the cis form unsaturated fatty acid of the residue (U).

The fat or oil (A) is fractionated into the crystal fraction (AF) in which G2U is concentrated and the liquid fraction (AL) in which GU2 is concentrated by crystallization and solid-liquid separation (the fractionation flow chart is shown in FIG. 1). At this time, the residual amount of a liquid component (the concentrations of GU2 and U3) in the crystal fraction can be reduced by separating a crystal fraction (BF) from a liquid fraction (BL) after mixing the crystal fraction (AF) obtained with the liquid G2U-containing fat or oil (B) whose GU2 concentration is lower than that of the liquid fraction (AL) fractionated by solid-liquid separation.

The suitable mixing ratio of the crystal fraction (AF) to the fat or oil (B) is in the range from 1:1 to 1:4, preferably 1:1 to 1:2. When the ratio of the fat or oil (B) to the crystal fraction (AF) is less than 1, sometimes, fractionation performance tends to be deteriorated because the ratio of the liquid component to the crystal component in the crystal fraction (AF) is too low, which results in a poor degree of mixing. When the ratio of the fat or oil (B) to the crystal fraction (AF) exceeds 4, on the other hand, G2U in the crystal fraction (AF) melts due to a high proportion of the liquid component, and the yield of the crystal fraction (BF) tends to be decreased. The degree of mixing and fractionation performance is further improved when the mixing ratio of the fat or oil (B) to the crystal fraction (AF) is in the range of 1 to 2.

When the crystal fraction (AF) is mixed with the fat or oil (B), preferably, the cake of the crystal fraction (AF) is crushed. The fractionation performance can be improved by mixing the crystal fraction (AF) and the fat or oil (B) by taking advantage of solubility of G2U and GU2 as well as U3. It is preferable to adjust the solubility of the crystal component (G2U) in the liquid component (GU2 and U3) to the content of the crystal component in the desired final product. An example for satisfying the above conditions is disintegration of the crystal fraction (AF) obtained by pressing at such a product temperature that the pressing has been carried out, followed by mixing the disintegrated crystal fraction with the warmed fat or oil (B).

While the fat or oil (B) is liquefied by warming when the crystal fraction (AF) is mixed with the fat or oil (B), the fat or oil (B) can be warmed according to G2U in the crystal fraction (AF), the molecular species of triglycerides of GU2, and its concentrations thereof. For example, in case that the triglyceride is 1,3-distearo-2-oleoyl triglyceride (StOSt), a suitable temperature of the product after mixing the crystal fraction (AF) with the fat or oil (B) is in the range from 34° C. to 36° C. In particular, when the crystal fraction (AF) at such a product temperature that the pressing has been carried out is mixed with the fat or oil (B) warmed at about 40° C., the time required for becoming the product temperature of 34 to 36° C. can be shortened and the quality and the yield of the desired final product after solid-liquid separation of the mixture can be improved.

As the liquid G2U-containing fat or oil (B) whose GU2 concentration is lower than that of the liquid fraction (AL) fractionated by solid-liquid separation, for example, the fat or oil (A) can be used. That is, the warmed fat or oil (B) in a liquid state scarcely dissolves the crystal component in the crystal fraction (AF) and replaces the liquid component in the crystal fraction (AF), thereby decreasing the concentration of GU2. Then, it is preferable that G and U are substantially the same as G and U in the crystal fraction (AF).

When the fat or oil (A) is used as the fat or oil (B) and mixed with the crystal fraction (AF), a part or all of the liquid fraction (BL) obtained by solid-liquid separation can be used for recycling.

The liquid fraction (AL) in which GU2 is concentrated can be used as a starting material for selective interesterification of the 1,3-positions. The above described interesterification reaction is a reaction using 1,3-position specific lipase as a catalyst. Since interesterification oil contains a large amount of triglycerides of GUG and GUU components, the crystal fraction (AF) containing more GUG component and the liquid fraction (AL) containing more GUU component can be obtained through solid-liquid separation by using this interesterification oil as a part or all of the fat or oil (A).

When the fat or oil (A) is used as the fat or oil (B), the liquid fraction (AL) and the liquid fraction (BL) can be used as starting materials of the interesterification reaction, or as a part or all of the fat or oil (A). Then, this reaction system affords an environmentally sound production system without discharging waste oil out of the reaction system.

While the fractionation method after solid-liquid separation is not particularly limited so long as the method is able to separate solids from liquids such as pressing, vacuum filtration and gravity filtration, the pressing is preferable from the view point of yields of the desired crystal fraction and liquid fraction, and the quality of the final product. The pressing pressure and pressing time can be adjusted according to the required quality of the crystal fraction after separation of the crystal fraction from the liquid fraction, and the degree of pressing (pressing pressure) is not particularly limited. The mesh size of the filter-clothes used for fractionation can be selected according to the crystal grain size of the crystal fraction, and is not particularly limited.

Hereinafter, the present invention will be explained in more detail by Examples. However, the present invention is not limited to Examples (numeric values, etc.).

Example 1

Preparation of Fat or Oil Containing G2U and GU2

Ethyl stearate and high-oleic sunflower oil were subjected to an interesterification reaction using 1,3-position specific lipase as a catalyst, and ethyl esters were removed by distillation to prepare interesterified oil (A1). The interesterified oil (containing StOSt, StOO, StStSt, StSt-DG, etc.) was completely melted at 50° C. or higher, solidified at 23° C. (product temperature 23° C.) and then subjected to solid-liquid separation by press filtration to obtain a crystal fraction (AF: yield 52%) and a liquid fraction (AL: yield 48%). The StOSt, StOO, StStSt and StSt-DG contents in the interesterified oil (A1), crystal fraction and liquid fraction are shown below. Each component was analyzed by high performance liquid chromatography.

TABLE 1

| | StOSt | StOO | StStSt | StSt-DG | Others |
|---|---|---|---|---|---|
| Interesterified oil (A1) | 41.3 | 25.3 | 0.9 | 2.5 | 30.0 |
| Crystal fraction (AF) | 68.5 | 9.0 | 1.6 | 1.4 | 29.5 |
| Liquid fraction (AL) | 9.8 | 45.4 | 0.5 | 4.6 | 39.7 |

The crystal fraction (AF) obtained by solid-liquid separation was disintegrated at 23° C. (the same temperature as the pressing temperature), and the crystal fraction as B was mixed with A1 which has been liquefied by warming at 40° C. (rapidly mixed at a mixing weight ratio of the crystal fraction (powdered AF):the interesterified oil (liquid A1)=1:1.5). Then, the mixture was allowed to stand for 30 minutes, and was press-filtered (pressing pressure of 2.9 MPa, pressing time of 60 minutes) with a filter press at room temperature of 35° C. (apparatus temperature) to obtain a crystal fraction BF and a liquid fraction BL. The results are shown in Table 2.

Comparative Example 1

According to the same manner as that in Example 1, the interesterified oil (A1) containing G2U and GU2 was used. The oil was completely melted at 50° C., subjected to crystal deposition by cooling, and press-filtered (pressing pressure of 2.9 MPa, pressing time of 90 minutes) with a filter press at room temperature corresponding to the final temperature of crystal deposition by cooling (apparatus temperature) of 23° C. The results are shown in Table 2.

TABLE 2

Results of measurement of components (G2U/GU2) and SFC % in crystal fractions in Example 1 and Comparative Example 1

| Crystal fraction | G2U Wt % | GU2 Wt % | SFC (26° C./40 hr) % 10° C. | 20° C. | 25° C. | 30° C. | 35° C. | Residual liquid ratio Wt % |
|---|---|---|---|---|---|---|---|---|
| Example 1 (BF) | 70.5 | 7.2 | 94.8 | 88.8 | 88.2 | 85.6 | 74.4 | 25.7 |
| Comparative Example 1 (AF) | 68.5 | 9.0 | 92.9 | 84.4 | 83.2 | 80.2 | 66.4 | 20.2 |

*) The components of G2U and GU2 were measured by high performance liquid chromatography

*) Residual liquid ratio: [(content of liquid component in crystal fraction)/(content of liquid component in liquid fraction)] × 100, where GU2 and U3 as liquid components.

Although the residual liquid ratio in Example is higher than that of Comparative Example by 5.5%, in the product of the present invention, the concentration of G2U in the crystal fraction is higher and the concentration of GU2 as the major component of the liquid fraction is reduced. This shows that fractionation performance is improved and the crystal fraction has good properties as hard butter.

As shown in FIG. 1, when the interesterified oil (A) was prepared by using the liquid fraction (BL) in place of high-oleic sunflower oil used for synthesizing the interesterified oil (A1) containing G2U and GU2, ethyl stearate obtained by fully hydrogenating ethyl oleate removed by distillation, and 1,3-position specific lipase as a catalyst, the same results as those in Example were obtained and a crystal fraction (BF) whose G2U concentration was increased and GU2 concentration was decreased was obtained. This fraction has suitable quality for hard butter.

Example 2

A middle-melting point fraction of palm oil (PMF: POP 46.2%, POL 5.7%, POO 14.4%, PPP 1.1%) was used as a starting material. After completely melting PMF at 70° C. or higher, the fat or oil was pre-cooled so that the product temperature was 22° C., and was crystallized at 20° C. for 24 hours to obtain crystal fraction 1. While a crystal fraction usually obtained by dry fractionation method is such crystal fraction 1, the crystal fraction 1 and liquid PMF pre-cooled at 22° C. were mixed in a weight ratio of 30:100, and the mixture was subjected to solid-liquid separation by press-filtration to obtain a crystal fraction 2 and a liquid fraction 2.

TABLE 3

| | Example 2 (crystal fraction 2) | Comparative Example 2 (crystal fraction 1) |
|---|---|---|
| POP | 66.6 | 65.6 |
| POL | 1.2 | 1.2 |
| POO | 3.1 | 4.1 |
| PPP | 2.3 | 2.2 |

The above results show that, in case of POP containing fat or oil obtained by fractionating palm mid fraction fat and oil, the crystal fraction 2 whose G2U (POP) concentration is increased and GU2 concentration is decreased is also obtained by separating into the crystal fraction and liquid fraction after mixing with liquid PMF as G2U (POP)-containing fat or oil (B). This shows that the crystal fraction 2 whose GU2 concentration was decreased was obtained, and this fraction had preferable quality as hard butter.

Figure 1:
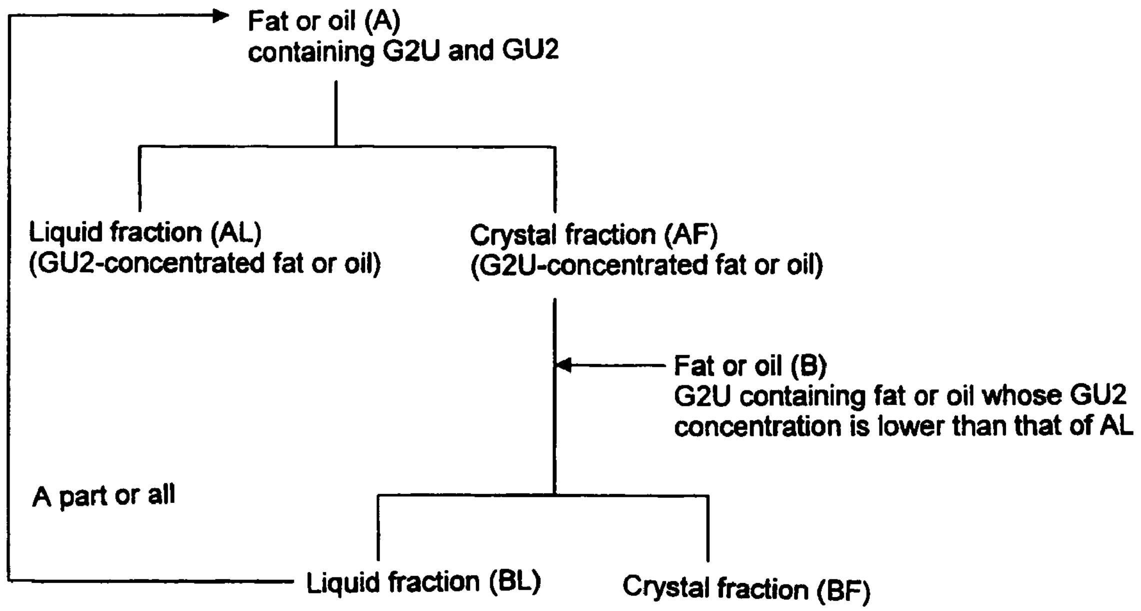
FIG. 1 is a flow chart of the dry fractionation of the present invention.

The invention claimed is:

1. A dry fractionation method of fat or oil which comprises the steps of:

fractionating fat or oil (A) containing G2U and GU2 through crystallization/solid-liquid separation into a cake of a crystal fraction of concentrated G2U (AF) and a liquid fraction of concentrated GU2 (AL), crushing the crystal fraction (AF) and mixing the crushed fraction with liquid G2U-containing fat or oil (B) whose GU2 concentration is lower than that of the liquid fraction (AL), and then separating the mixture into a crystal fraction (BF) and a liquid fraction (BL), wherein G represents a saturated or trans acid form fatty acid residue, U represents a cis form unsaturated fatty acid residue, G2U represents a triglyceride of two G-residues and one U-residue bonded together, and GU2 represents a triglyceride of one G-residue and two U-residues bonded together, and wherein the fat or oil (A) is vegetable butter or a middle-melting point fraction thereof, interesterified oil obtained by selectively introducing a saturated fatty acid to 1,3-positions of fat or oil which is rich in oleic acid at the 2-position, or isomerized hydrogenated oil.

2. The fractionation method according to claim 1, wherein liquid G2U-containing fat or oil (B) whose GU2 concentration is lower than that of the liquid fraction (AL) is the fat or oil (A).

3. The fractionation method according to claim 1, wherein the liquid fraction (BL) is used by recycling as a part or all of the fat or oil (A).

4. The fractionation method according to claim 1, wherein the vegetable butter is palm oil, shea butter or illipe butter.

5. The dry fractionation method according to claim 1, wherein G2U is 1 ,3-di-saturated-2-unsaturated triglyceride (SUS, where S represents a saturated fatty acid residue and U represents a cis form unsaturated fatty acid residue).

6. The dry fractionation method according to claim 5, wherein the saturated fatty acid residue (5) has 16 to 22 carbon atoms, and the unsaturated fatty acid residue (U) has 18 carbon atoms.

7. The fractionation method according to claim 3, wherein the fat or oil (A) is interesterified oil whose starting material is the liquid fraction (AL).

8. The fractionation method according to claim 1, wherein the mixing ratio of the crystal fraction (AF) to the fat or oil (B) is in the range from 1:1 to 1:4.

9. The fractionation method according to claim 7, wherein the mixing ratio of the crystal fraction (AF) to the fat or oil (B) is in the range from 1:1 to 1:2.

10. The fractionation method according to claim 1, wherein the temperature-controlled fat or oil (B) is mixed with the crystal fraction (AF).

11. The dry fractionation method according to claim 2, wherein G2U is 1 ,3-di-saturated-2-unsaturated triglyceride (SUS, where S represents a saturated fatty acid residue and U represents a cis form unsaturated fatty acid residue).

* * * * *